US005567122A

United States Patent [19]

Schulte

[11] Patent Number: 5,567,122

[45] Date of Patent: Oct. 22, 1996

[54] CYLINDER PUMP HAVING CONTROLLABLE PISTON/DRIVE DETACHMENT

[75] Inventor: Harvey Schulte, Los Altos, Calif.

[73] Assignee: Barry J. Walter, Fremont, Calif.

[21] Appl. No.: 322,214

[22] Filed: Oct. 13, 1994

[51] Int. Cl.[6] .............................. F04B 49/00; A61M 5/20

[52] U.S. Cl. .......................... 417/214; 417/223; 417/415; 417/521; 128/DIG. 1

[58] Field of Search .................................... 417/214, 216, 417/223, 415, 539, 419, 521; 92/14; 128/DIG. 1; 604/152, 118, 120, 121, 131

[56] References Cited

U.S. PATENT DOCUMENTS

| | | | |
|---|---|---|---|
| 3,155,090 | 11/1964 | Holter | 128/DIG. 1 |
| 4,127,360 | 11/1978 | Carpenter | 417/419 |
| 4,155,490 | 5/1979 | Glenn | 128/DIG. 1 |
| 4,563,175 | 1/1986 | LaFond . | |
| 4,666,430 | 5/1987 | Brown et al. . | |
| 4,769,009 | 9/1988 | Dykstra | 128/DIG. 1 |
| 4,833,384 | 5/1989 | Munro et al. | 128/DIG. 1 |
| 4,846,797 | 7/1989 | Howson et al. | 128/DIG. 1 |
| 5,100,380 | 3/1992 | Epstein et al. . | |
| 5,176,646 | 1/1993 | Kuroda | 604/131 |

FOREIGN PATENT DOCUMENTS

| | | | |
|---|---|---|---|
| 866988 | 2/1953 | Germany | 604/131 |
| 2809990 | 9/1978 | Germany | 128/DIG. 1 |

*Primary Examiner*—Timothy Thorpe
*Assistant Examiner*—Roland G. McAndrews, Jr.

[57] ABSTRACT

A cylinder pump having a controllable piston/drive detachment is disclosed that can engage or disengage a piston rod using a solenoid. Most any type of drive can be used. The cylinder pump could have one or more cylinders. Each cylinder and piston rod has quick connect and disconnect mountings. The cylinder pump could be a syringe pump or drive.

22 Claims, 5 Drawing Sheets

CYLINDER PUMP HAVING CONTROLLABLE PISTON/DRIVE DETACHMENT

FIELD OF THE INVENTION

This invention is directed to the field of fluid handling, and more particularly, to a novel cylinder pump having a controllable piston/drive detachment which the user can select meter and deliver fluid from one or more cylinders which are quick connect/disconnect.

BACKGROUND OF THE INVENTION

This invention relates to fluid handling. There are applications where it is advantageous to engage or disengage piston rods to control the flow of a fluid. There are also applications where more than one fluid is needed to be metered and delivered at a time. A few such applications are in sample preparation instruments for blood, serum and urine. Reagents and other chemicals are added to the sample to prepare it for analysis. Heretofore, there were two common systems to add more than one fluid to the sample. The first means was to have a separate motor and pump for each fluid to be added. This provided a lot of flexibility but at a high price. It also made the apparatus complex, large and heavy. The second means was to use one motor and pump but to equally stroke a mechanically connected bank of syringes. The diameter of the syringes in the bank could be varied so they could deliver different flow rates or volumes for the same stroke. This costs less than the first means but is much less flexible and makes it difficult and time consuming to vary which fluids are being delivered and in what volumes because syringes must be manually changed or removed. Accordingly it would be desirable to select which syringes will deliver fluid, to easily and quickly change the syringes and to have a smaller, less complex and lower cost drive means.

SUMMARY OF THE INVENTION

The novel fluid handling apparatus of the present invention is a cylinder pump having a controllable piston/drive detachment with means to accurately stroke one or more pistons at a time while keeping the fluids separate. There is only one drive means required and neither the mechanical, electrical, electronic nor software designs are complex. The simplicity of the design will result in a lower cost but equally accurate system as compared to the state of the art. The volume delivered is simply the stroke times the area of the syringe bore. Only one of many possible embodiments is described in detail in this specification, The major components of the preferred embodiment consists of a stepper motor, lead screw, multiple cylinders/pistons or syringes, a solenoid for each cylinder/piston or syringe and a controller. Different diameter pistons/cylinders and syringes can be used to vary the flow rate for the same stroke and the present invention allows quick and easy replacement using standard disposable or laboratory syringes.

An actual application of this embodiment is in the field of flow cytometry where reagents and other chemicals are added to a blood sample to prepare it for analysis. For example, blood is put into one or more test tubes that will later be used in an analysis machine. Another syringe is used to add a reagent to the test tube(s) to lyse the red blood cells. Still another syringe is used to add another reagent depending on what tests are to be performed. All these syringes are driven by the same motor through a block that mounts or houses solenoid valves to engage or disengage syringes as required. Therefore during an actuation of the block by the stepper motor and lead screw the user can specify having all, some or none of the syringes selectively stroked to deliver only what fluid and in what quantity it is required. This provides the user previously unavailable flexibility with simple, compact and low cost hardware and software.

BRIEF DESCRIPTION OF THE DRAWINGS

Other features and advantages of the present invention will became apparent as the invention becomes better understood by referring to the following exemplary and nonlimiting detailed description of the preferred embodiments and to the drawings, wherein.

REFERENCE NUMERALS IN DRAWINGS

| | | | | | |
|---|---|---|---|---|---|
| 10 | pump | 12 | syringe | 13 | orifice |
| 14 | shaft | 15 | piston rod | 16 | frame |
| 18 | block | 19 | piston | 20 | slot |
| 22 | connector | 23 | cylinder wall | 24 | lead screw |
| 26 | solenoid | 27 | solenoid pin | 28 | rod pin |
| 30 | rod extension | 36 | screw | 37 | mount |
| 38 | cavity | 39 | hole | 40 | valve |
| 42 | tube | 44 | drive means | 45 | motor wires |
| 46 | belt | 48 | pulley | 50 | sensor |
| 51 | receiving hole | 52 | controller | 53 | sensor wires |
| 54 | link | 55 | groove | 56 | pin spring |
| 57 | link pin | 58 | rack | 60 | pinion |
| 62 | channel | 64 | linear transducer | | |

DETAILED DESCRIPTION OF THE PREFERRED EMBODIMENTS

Figure 1:
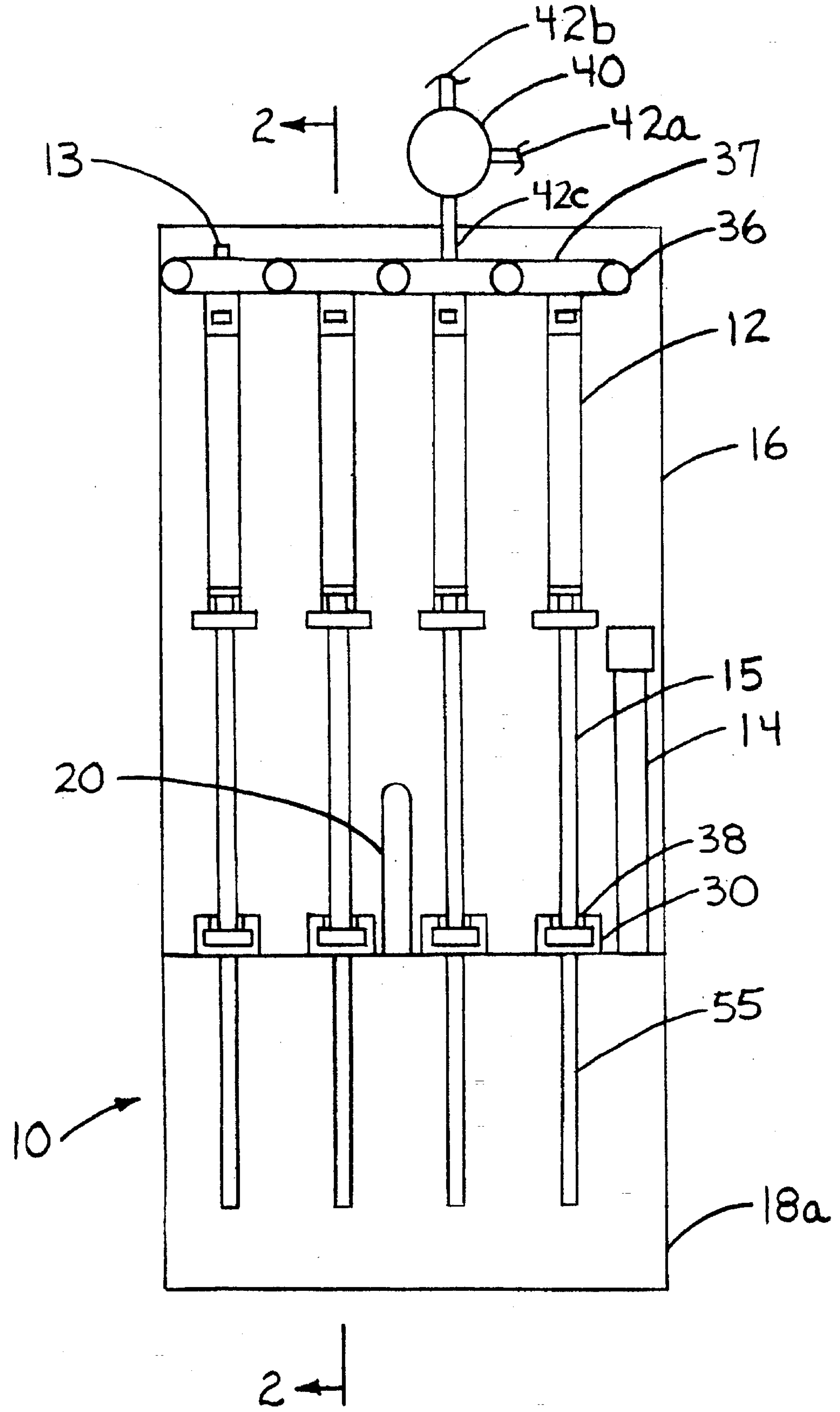
FIG. 1 is a front view of the syringe pump of the present invention.
Figure 2:
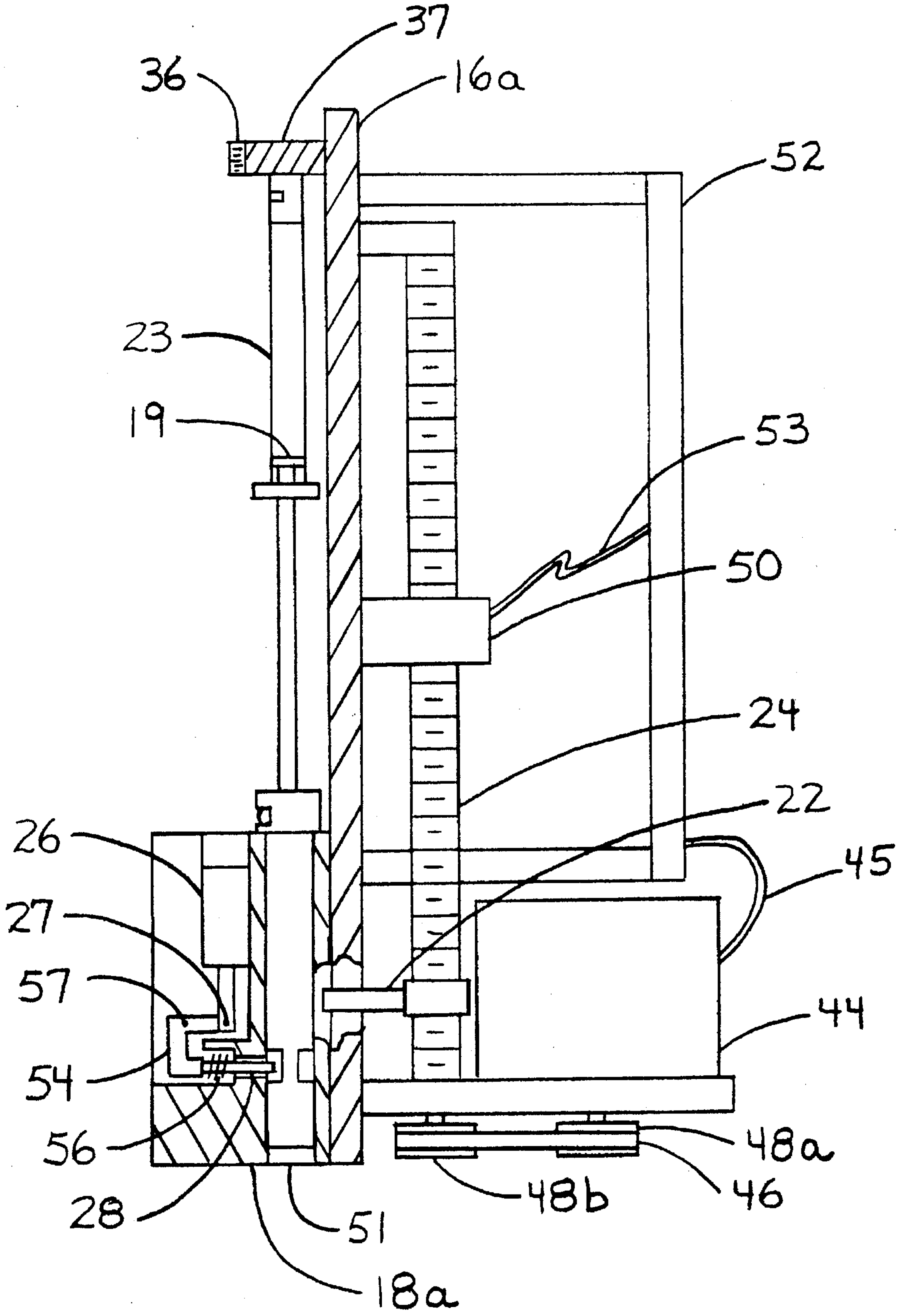
FIG. 2 is a cross-sectional view of the syringe pump of FIG. 1 taken along lines 2—2.
Figure 5:
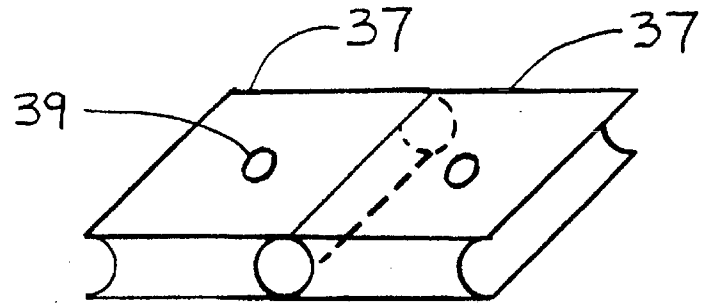
FIG. 5 is a perspective view of the top quick connect/disconnect mount.
Figure 6:
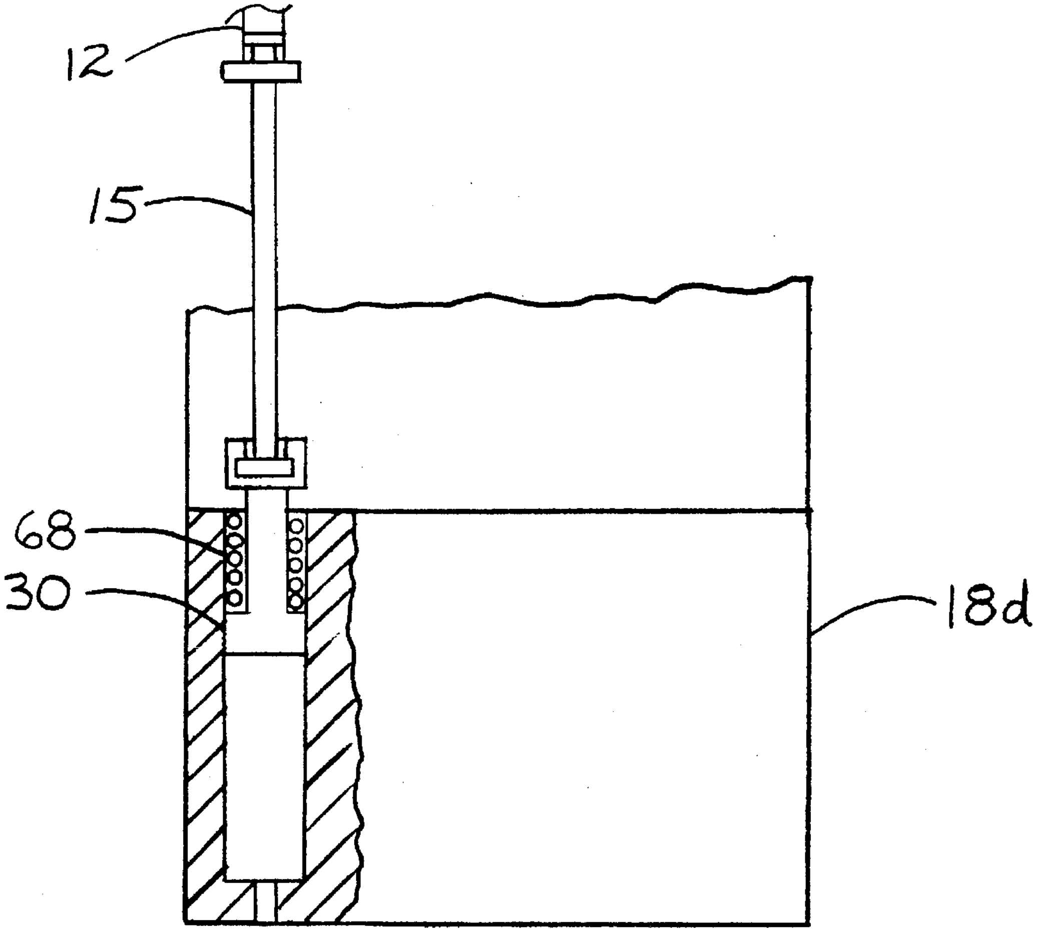
FIG. 6 is a cut away front view of a fluid drive means.

FIG. 1 is a front view of a four syringe pump apparatus 10 incorporating certain aspects of the present invention. Said apparatus can be built for one or more syringes 12 with top orifice 13 and piston rod 15. A piston and cylinder could replace a syringe 12 in a different embodiment. FIG. 2 is a substantially cut away view of apparatus 10 taken along cut lines 2—2. The frame **16*a* is for mounting the various components that remain fixed to the frame 16*a*. Block 18*a* moves relative to frame 16*a* with the drive motion provided through slot 20 and guided by shaft 14 shown in FIG. 1 via connector 2 2 attached to the lead screw 24 shown in FIG. 2. A clearance is maintained between block 18*a* and frame 16*a*. Continuing to refer to FIG. 2, the means of being able to independently engage or disengage rod pins 28 make it possible to stroke all, some or none of the rod extensions 30. Rod extensions 30 can be square, circular or any other cross-section. Rotation will be prevented if other than a circular cross-section is used. Rotation can be also prevented by use of a longitudinal slot in rod extensions 30 and aligned fixed pins in block 18*a* that slide in longitudinal slots in rod extensions 30. Non-rotation during operation will assure that rod extensions will always be in an orientation for easy removal of syringes 12. The invention relies on the friction between the piston 19 and cylinder wall 23 being greater than between the rod extension 30 and the rod extension receiving hole 51. This is necessary so piston 19 stays in position when corresponding rod extension 30 is not engaged and moving with the block 18***a*. This is not a problem since there must be a very small clearance to prevent leakage between piston 19 and cylinder wall 23. The clearance between rod extension 30 and rod extension receiving hole 51 can be relatively large. In this embodiment, rod pins 28 are moved by electrical solenoids 26. The individual syringes 12 can contain the same or different fluids and can be the same or different diameters. Different diameter syringes 12 will vary the volume delivered for the same stroke. Quick disconnect screw 36, mount 37 and cavity 38 on rod extension 30 allow the user to quickly and easily change syringes 12. This embodiment uses manual style syringes 12 with a piston rod end in the shape of a disk. The invention with minor modifications can use instrumentation style syringes 12 that have a hole perpendicular to the direction of travel to fit over a pin on the rod extension top end. This quick connect and disconnect feature is also applicable to a piston and cylinder combination. Referring to FIG. 5, shown is one possible embodiment of quick connect and disconnect mount 37, a small rectangular structural piece with two concave sides that provide clearance for screw 36 shown installed in FIG. 1. Still referring to FIG. 1, mount 37 is rigidly attached to the tip of the syringe 12 through hole 39 shown in FIG. 7 and if using a threaded adapter remains with syringe 12 when it is removed. The syringe 12 can be as easily removed upwards as outwards. Mount 37 and support 35 could be built to slide in and out and up and down to adapt to different size syringes. Referring to FIG. 1, valve 40 could be included in the assembly to minimize loss of fluid when the tube 42*c* is disconnected and to allow continuous operation by aspirating fluid via tube 42*a* and evacuating and metering fluid out via tube 42*b*. Valve 40 could include pinch valves, check valves, or actuated valves to direct the flow. A multiple syringe pump apparatus 10 would preferably use standard length syringes 12 in order to provide greatest flexibility, modularity and therefore speed of changeover. Referring to FIG. 2, the drive means 44 can accurately move in increments. The drive means 44 can be linear, rotary, electrical, hydraulic or pneumatic. Shown is a common industry means to drive a syringe pump using a rotary stepper motor for drive means 44 with its rotary motion being translated into linear motion by lead screw 24 through belt 46 and pulleys 48*a* and 48*b*. One manufacturer uses gears instead of pulleys. The travel of lead-screw 24 can be measured by the sensor 50 that sends a signal to a controller 52 via wires 53. The controller 52 uses this signal to adjust the travel to improve the accuracy of the stroke length and therefore improve the accuracy of the delivered volume. This accuracy correction is desirable due to motor inaccuracy, belt drive inaccuracy and lead screw backlash. Controller 52 also converts manual user commands into signals to the drive means 44. Block 18*a* is manufactured with cavities to contain certain components. Shown in FIG. 2, solenoid 26 is rigidly installed in a cylindrical hole in block 18*a* and receives electrical signals from controller 52 to move link 54 through solenoid pin 27. When assembling this apparatus, link 54 is installed through groove 55 in block 18*a*. Link pin 57 attaches link 54 to block 18*a*. When solenoid 26 is energized, link 54 pivots around link pin 57 and overcomes the resistance of pin spring 56 to move rod pin 28 to engage rod extension 30. Another embodiment could show solenoid 26 perpendicular to the travel direction of block 18*a*. In this embodiment, solenoid 26 could engage rod extension 30 directly without the need for link 54. The disadvantage to the perpendicular arrangement is that block 18*a* has to be larger in depth than in the embodiment shown. Alternatively, rod pin 28 could be actuated by air or fluid conveyed in passageways in a block similar to block 18*a* and valves (not shown) that direct the air or fluid only to the pin bores that correspond to the syringes 12 to be stroked. There is no need to provide an airtight seal between the bore and the rod pin 28. For example, a small clearance will not leak enough air to prevent the rod pin 28 from moving with normal laboratory air pressure. In the embodiment shown in FIG. 2, pin spring 56 holds rod pin 28 disengaged from rod extension 30 when there is no signal being sent to solenoid 26. When rod pin 28 is engaged, it fits into the slot or hole in rod extension 30 which slides in rod extension receiving hole 51 parallel and next to corresponding solenoid 26. There are at least three other arrangements to use solenoid 26 to engage rod extension 30. Solenoid 26 could be mounted parallel but below rod extension 30 with pin spring 56 in line with the axis of solenoid 26 but on the other side of a link similar to link 54. In another variation, solenoid 26 could be mounted parallel and next to rod extension 30 with spring 56 in line and on the same side of a pivoting link similar to link 54. Still another variation could have solenoid 26 mounted in line and below rod extension 30. Other applications might not use solenoid 26 at all to engage and disengage rod pin 28 but use air pressure as described above. Even a manual means could be used to engage and disengage rod extension 30. Manual means of engagement and disengagement could be used for a very low cost version of the pump apparatus 10. A standard quarter turn spring loaded fastener with an elongated pin could be mounted to the vertical surface of block 18*a* and used to manually engage or disengage rod extension 30. Another alternative is to use an over center latch that would rotate into engagement with rod extension 30. All these arrangements are practical and their use depends on the particular needs of the application.

There are a number of variations possible to reduce the size and cost of the pump apparatus shown in FIGS. 1 and 2. A block similar to block 18 a could be fabricated with aligned and threaded holes that engage directly with lead screw 24 eliminating connector 22.

Figure 3:
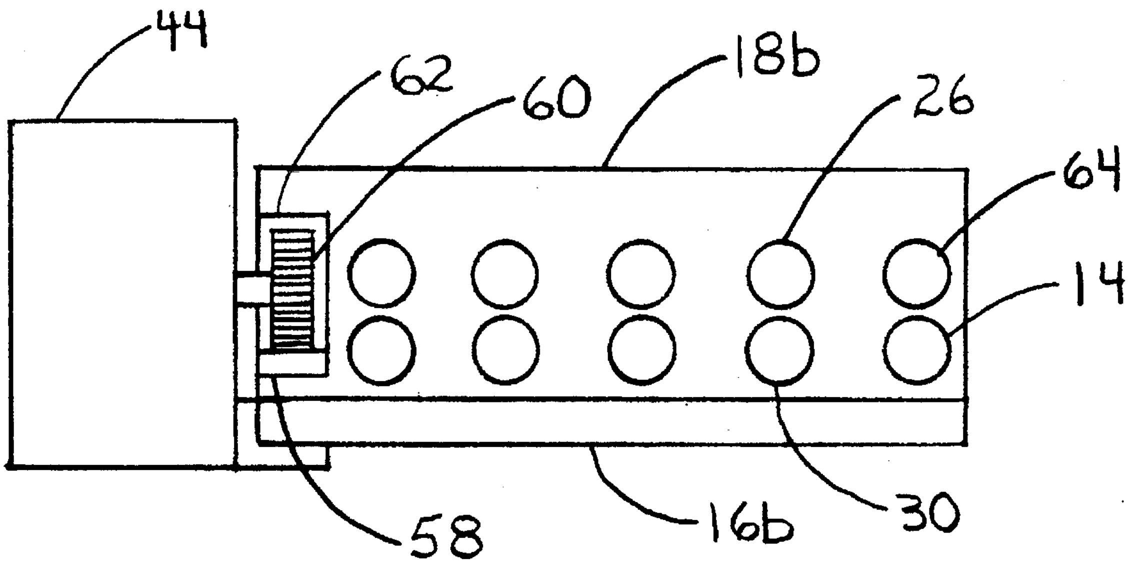
FIG. 3 is a view of a rack and pinion drive means.
Figure 4:
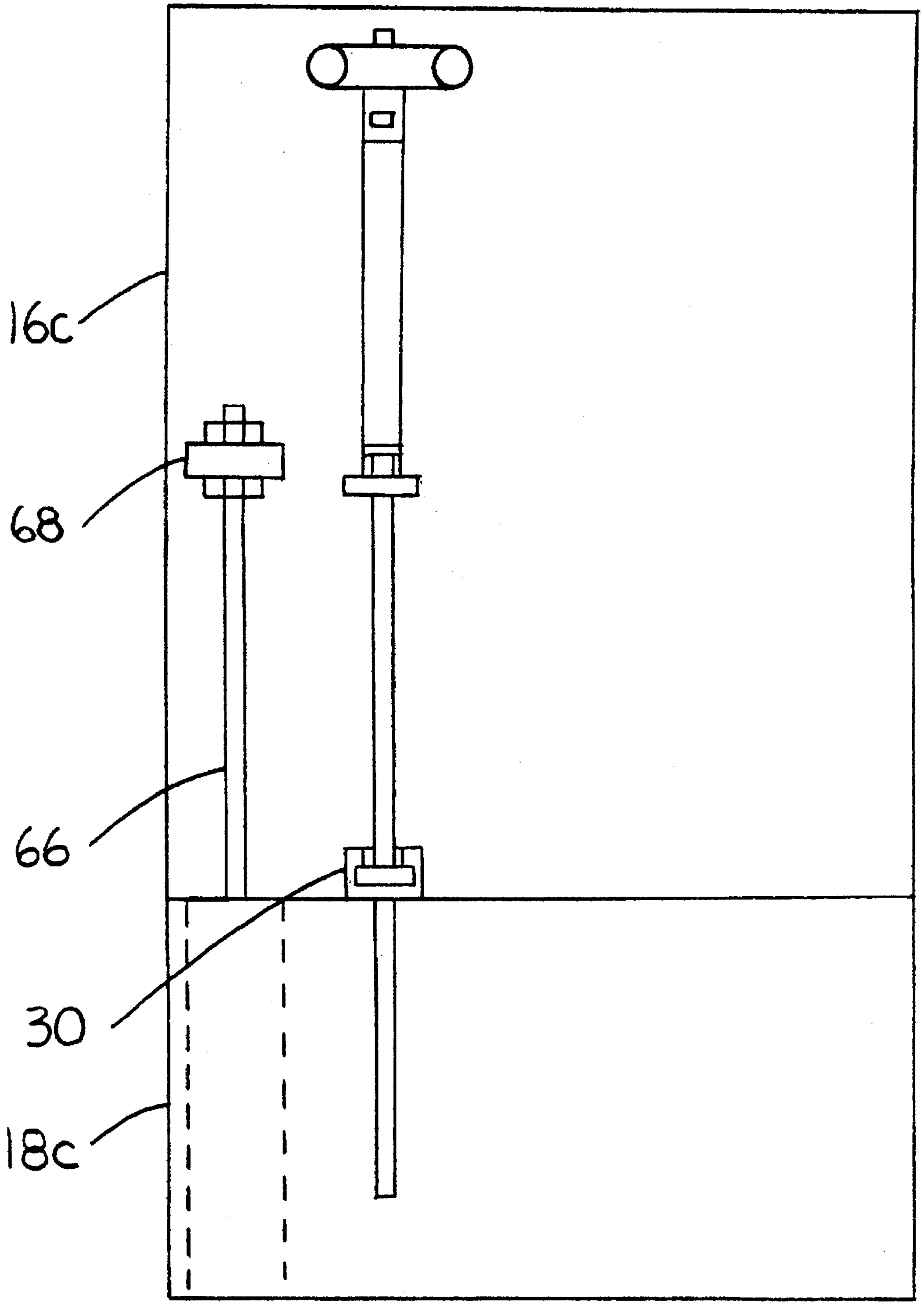
FIG. 4 is a view of a linear actuator drive means.

FIG. 3 is a bottom view of a drive means using a rack 58 and a pinion 60 to eliminate the need for lead screw 24, connector 22, belt 46, pulleys 48 and possibly sensor 50 shown in FIG. 2. Block 18*b* would be similar to block 18 a except it would have channel 62 running the length of block 18*b* to mount rack 58 and provide clearance for pinion 60. The drive means 44 could also be mounted perpendicular to the direction shown in FIG. 3 and drive the block 18*b* through frame 16*b*. Frame 16*b* would be similar to frame 16*a* except for the mounting of drive means 44 and controller 52 in FIG. 2. A direct drive arrangement like this may be accurate enough without a closed loop feedback signal. If it is not accurate enough without a feedback signal, a linear transducer 64 could be mounted in a receiving hole next to shaft 14. This arrangement would significantly reduce the complexity and size of pump 10 shown in FIGS. 1 and 2.

The different drive means shown in FIG. 3 is not an entirely new drive means but now becomes attractive for this application because of the addition of sliding block 18*b* in FIG. 3. Now provided is a surface to mount the rack 58 in FIG. 3. This arrangement would certainly provide a less complex, smaller size and lower cost apparatus than is currently being used for multiple syringe pumps 10.

OPERATION OF INVENTION

Apparatus 10 in FIGS. 1 and 2 is operated based on input from the user. The user commands can be inputted through a keypad, switches, touch sensitive screen, mouse, keyboard or other user interface device (not shown). In the embodiment shown, the cycle starts at the top of the stroke placing the large diameter coupling elements of rod extensions 30 in contact with block 18*a*. Having the large diameter coupling elements of rod extensions in contact with block 18*a* is a simplified means to align the holes or slots in rod extensions 30 with pins 28. Holes and slots could be put in other locations also so pins 28 could be engaged at different or multiple positions. Syringes 12 can be empty, partially full or entirely full at the start of a cycle. When pins 28 are aligned with the holes or slots in rod extensions 30, controller 52 sends signals to energize selected solenoids 26. Controller 52 is used to send a signal to rotate drive means 44 a certain amount either to align pins 28 with slots in rod extensions 30 or to start a cycle. The drive means 44 rotation causes lead screw 24 to rotate and connector 22 to linearly travel a proportional amount. An optional sensor 50 can monitor the actual linear travel and provide a feedback signal through wires 53 to controller 52. Based on the feedback signal, controller 52 can adjust the rotation of drive means 44 in order to have a precise amount of travel. Connector 22 drives block 18 a that houses solenoids 26. Any rod extensions 30 that have not had their corresponding solenoids 26 engaged will not move with the block 18*a* in the aspiration mode. If the cycle started at the top of the stroke, disengaged rod extensions 30 will also not move in the dispense mode because due to friction they will hang from the fully compressed syringe. To disengage solenoid 26, no electrical power is sent to solenoid 26 and spring 56 retracts rod pin 28. When block 18*a* travels, rod extension 30 corresponding to disengaged rod pin 28 will not stroke if the cycle started at the top of the stroke. To engage solenoid 26, electrical power is sent from the controller 52 so solenoid 26 causes the rod pin 28 to overcome the force of spring 56 and engage rod pin 28 into the hole or slot on rod extension 30. Engaged solenoids 26 cause their corresponding rod extensions 30 to travel with block 18*a*. The signal to stop drive means 44 comes from controller 52 using original input parameters and the sensor feedback signal. The sequence can be repeated with the same or different parameters. The remaining volume of fluid in each syringe 12 can be sensed directly or derived by knowing how much was put into the syringe 12 at the start and how much has been used. This can be a manual calculation or programmed into controller 52. The drive means 4 4 has the capability to travel in either direction so it can return block 18*a* to its lower most position where full syringes 12 can be installed. There is also an option to install and use valve 40 to supply fluid from a reservoir (not shown) connected to tube 42*a* and pump a metered amount of fluid through tube 42*b*.

Thus the reader will see that the invention described above provides a simple, relatively small, low cost but equally flexible alternative to using a separate drive motor for each syringe 12. It provides better accuracy and inherent safety than an apparatus that operates on high pressure compressible fluids. The invention also keeps the fluids pumped by each syringe 12 completely separate thereby eliminating the possibility of cross-contamination. Also included is a quick connect and disconnect feature to change syringe 12 sizes or fluids being pumped. In a multiple syringe pump application, standard syringe sizes from existing manufacturers can be used without modifications or adjustments to the apparatus 10.

Although the invention was developed for and the embodiments shown describe a multiple syringe pump having controllable piston/drive detachment, the teachings of the invention are not to be considered so limited. Rather, the teachings of the invention apply to any type of cylinder and piston in either the evacuation or aspiration pump mode. Many other variations are possible and a few were described above. For example, the rod extensions 30 could be engaged in a number of ways using solenoid 26 or in a lower cost machine even actuated by hand. There could be any number of syringes 12 used in an application of this invention and in any geometry. For example, multiple cylinders 23 or syringes 12 in FIG. 2 could be arranged in a circular fashion and the principles could still be applied. The apparatus 10 could be operated in any orientation. Accordingly, the scope of the inventions should be determined not by the embodiments illustrated, but by the appended claims and their legal equivalents.

I claim:

1. A cylinder pump, said cylinder pump including an interior piston with attached piston rod and an exterior cylinder wall having top and bottom ends, a fluid orifice disposed on said top end and a rod opening on said bottom end wherein said piston rod passes therethrough, said cylinder pump comprising:

a) a frame having an orifice seat means for receiving said fluid orifice and placing said cylinder in fluid communication with a predetermined fluid depository;

b) a movable rod engagement means slidably disposed on said frame which selectively engages and disengages said piston rod;

c) drive means disposed on said frame for movement of said rod engagement means.

2. The cylinder pump of claim 1 wherein the movable rod engagement means includes a block having a rod extension receiver hole disposed therein.

3. The cylinder pump of claim 2, including a rod extension connected to the piston rod and slidably disposed within said rod extension receiver hole, said rod extension having a top portion and bottom portion, said bottom portion having a pin receiver opening disposed therein.

4. The cylinder pump of claim 3 wherein said piston rod terminates in a shaped end, and said rod extension further including a shaped receiver opening disposed in the top portion of said rod extension for receiving said shaped end to provide a quick connect/disconnect with said piston rod, said rod extension further including a means to prevent rotation to assure said receiver opening remains in a position to allow easy replacement of said cylinders and pistons.

5. The cylinder pump of claim 4 wherein the movable rod engagement means further includes a mount to provide a quick connect and disconnect with said cylinder.

6. The cylinder pump of claim 4 wherein the movable rod engagement means further includes an engagement pin and an engagement pin movement means for moving said engaging pin so as to mechanically engage and disengage said block and said rod extension by inserting and withdrawing said engagement pin within said pin receiver opening when said engagement pin movement means moves said pin.

7. The cylinder pump of claim 6 wherein the movable rod engagement means further includes an electrical solenoid and an engagement pin cooperatively disposed in said block to provide for mechanical engagement and disengagement of said block and said rod extension by inserting and withdrawing said engagement pin within said pin receiver opening when said electrical solenoid is energized and de-energized.

8. The cylinder pump of claim 7 wherein the drive means includes drive train means for moving said block forward and reverse in a direction so as to evacuate and aspirate said cylinder respectively.

9. The cylinder pump of claim 8 wherein the drive train means includes a stepper motor and a lead screw drive.

10. The cylinder pump of claim 8 wherein the drive train means includes a rack and pinion drive.

11. The cylinder pump of claim 1 wherein the cylinder and piston are a syringe.

12. A multiple cylinder pump, said multiple cylinder pump including interior pistons with attached piston rods and exterior cylinder walls having top and bottom ends, with fluid orifices disposed on said top ends and rod openings on said bottom ends wherein said piston rods pass therethrough, said multiple cylinder pump comprising:

a) a frame having at least a first and second orifice seat means for receiving said fluid orifices of at least first and second cylinders respectively and for placing said first and second at least a first and second pistons in fluid communication with predetermined fluid depositories;

b) a movable rod engagement means slidably disposed on said frame which selectively engages and disengages each of said piston rods, respectively; and c) drive means disposed on said frame for movement of said rod engagement mean.

13. The multiple cylinder pump of claim 12 wherein the moveable rod engagement means includes a block having at least a first and second rod extension receiver holes disposed therein.

14. The multiple cylinder pump of claim 13 including first and second rod extensions connected to piston rods and slidably disposed in said first and second rod extension receiver holes respectfully, said first and second rod extensions each having a top portion and a bottom portion, each of said bottom portions having first and second pin receiver openings disposed therein respectively.

15. The multiple cylinder pump of claim 14 wherein each of said piston rods terminate in a shaped end and said rod extensions each including a receiver opening disposed in the top portion of said first and second rod extensions, said shaped receiver openings being adapted for receiving said shaped ends to provide a quick connect/disconnect between said piston rods and said rod extensions, said rod extension further including a means to prevent rotation to assure said receiver slot remains in a position to allow easy replacement of said cylinders and pistons.

16. The multiple cylinder pump of claim 15 wherein the movable rod engagement means further includes mounts to provide a quick connect and disconnect with said cylinders.

17. The multiple cylinder pump of claim 15 wherein the movable rod engagement means further includes at least a first and second engagement pins and at least a first and second engagement pin movement means for moving said first and second engagement pins so as to mechanically engage and disengage between said block and each of said first and second rod extensions by selectively inserting and withdrawing each of said first and second engagement pins within said first and second pin receiver openings when said first and second engagement pin movement means moves said first and second pin, respectively.

18. The multiple cylinder pump of claim 17 wherein the movable rod engagement means further includes at least a first and second electric solenoids and said first and second engagement pins cooperatively disposed in said block to provide for mechanical engagement and disengagement between said block and each of said first and second rod extensions by selectively inserting and withdrawing each of said first and second engagement pins within said first and second pin receiver openings when said first and second electric solenoids are energized and de-energized respectively.

19. The multiple cylinder pump of claim 18 wherein the drive means includes drive train means for moving said block forward and reverse in* a direction to evacuate and aspirate each of said first and second cylinders respectively.

20. The multiple cylinder pump of claim 19 wherein the drive train means includes a stepper motor and lead screw drive.

21. The multiple cylinder pump of claim 19 wherein the drive train means includes a rack and pinion drive.

22. The multiple cylinder pump of claim 12 wherein the cylinders and pistons are syringes.

* * * * *